US010478572B2

(12) United States Patent
Ventura et al.

(10) Patent No.: US 10,478,572 B2
(45) Date of Patent: Nov. 19, 2019

(54) POWDER COMPARTMENT FOR HIGH DOSAGE DRUG DELIVERY

(71) Applicant: Hovione Technology Limited, Co Cork (IE)

(72) Inventors: João Ventura, Loures (PT); Peter Villax, Loures (PT)

(73) Assignee: Hovione Technology Ltd., Cork (IE)

( * ) Notice: Subject to any disclaimer, the term of this patent is extended or adjusted under 35 U.S.C. 154(b) by 192 days.

(21) Appl. No.: 15/117,571

(22) PCT Filed: Apr. 28, 2016

(86) PCT No.: PCT/GB2016/051073
§ 371 (c)(1),
(2) Date: Aug. 9, 2016

(87) PCT Pub. No.: WO2016/174393
PCT Pub. Date: Nov. 3, 2016

(65) Prior Publication Data
US 2018/0036497 A1 Feb. 8, 2018

(30) Foreign Application Priority Data
Apr. 30, 2015 (PT) .................................. 108426

(51) Int. Cl.
*A61M 15/00* (2006.01)
*A61K 9/00* (2006.01)

(52) U.S. Cl.
CPC .......... *A61M 15/002* (2014.02); *A61K 9/0075* (2013.01); *A61M 15/0021* (2014.02);
(Continued)

(58) Field of Classification Search
CPC ............ A61M 15/002; A61M 15/0021; A61M 15/0023; A61M 15/0025; A61M 15/0026;
(Continued)

(56) References Cited

U.S. PATENT DOCUMENTS 5,787,881 A * 8/1998 Chawla ............. A61M 15/0028
128/203.15
2007/0283955 A1 12/2007 Tsutsui
(Continued)

FOREIGN PATENT DOCUMENTS

EP 1106196 6/2001
GB 2253200 9/1992
(Continued)

OTHER PUBLICATIONS

PCT/GB2016/051073 ISR and Written Opinion dated Jul. 12, 2016, 14 pages.
(Continued)

*Primary Examiner* — Jan Christopher L Merene
*Assistant Examiner* — Elliot S Ruddie
(74) *Attorney, Agent, or Firm* — Blank Rome LLP

(57) ABSTRACT

A dry powder inhaler for pulmonary or nasal use, comprising at least an inhaler body 801 and a cartridge 803 with at least one powder compartment 805 including one dose of a drug. The body has an opening 804 shaped for receiving the cartridge 803 and the means to allow a controlled sliding movement of the cartridge 803 relative to the body 801 after mounting. The cartridge powder compartment 805 comprises at least two inlets or slits 806, 809, at least one of which is a side inlet 809, for the admission of air, and a compartment outlet 807 to allow filling and fluid communication with an inhalation channel 808 provided in the body 801. In use, the patient slides the cartridge 803 relative to the body 801 from the storage position, where the inlets in the cartridge powder compartment 805 are blocked and sealed by walls comprised in the body 801, into the inhalation position, where the compartment inlets become available for the admission of air used in the dispersion of the particles there contained and the compartment outlet 807 becomes
(Continued)

Figure 2A:
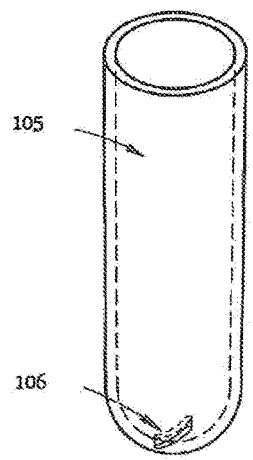
Figure 2B:
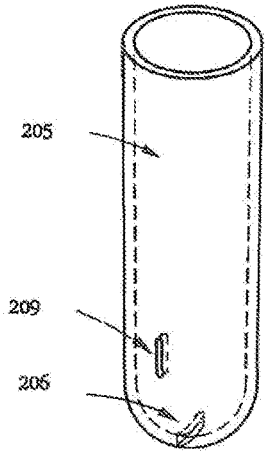
Figure 2C:
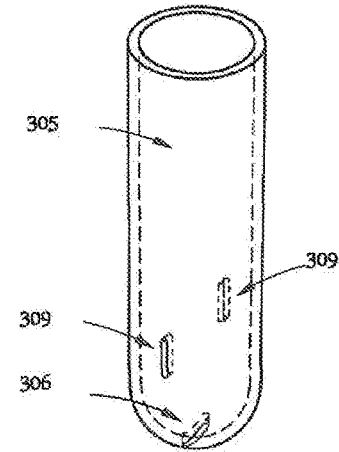
Figure 2D:
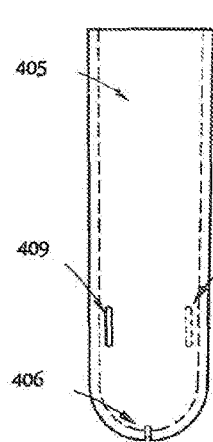
Figure 2E:

aligned with the inhalation channel 808 in the body 801 to allow the entrainment of the dose dispersed through the device and into the desired site of action during inhalation. The addition of one or more lateral vents 809 in the cartridge powder compartments induces a turbulent and swirling flow pattern that promotes improved dispersion and entrainment. The invention affords a very economical and simple device for the delivery of high dosages of inhaled medicines.

13 Claims, 6 Drawing Sheets

(52) U.S. Cl.
CPC .... *A61M 15/0028* (2013.01); *A61M 15/0086* (2013.01); *A61M 15/0043* (2014.02); *A61M 2202/064* (2013.01)

(58) Field of Classification Search
CPC ............ A61M 15/0028; A61M 15/003; A61M 15/0031; A61M 15/0033; A61M 15/0035; A61M 15/0036; A61M 15/0038; A61M 15/004; A61M 15/0041; A61M 15/0045; A61M 15/0046; A61M 15/0048; A61M 15/0086; A61M 2202/06; A61M 2202/064; A61K 9/007; A61K 9/0073; A61K 9/0075
See application file for complete search history.

(56) References Cited

U.S. PATENT DOCUMENTS

| | | | |
|---|---|---|---|
| 2009/0178676 A1* | 7/2009 | Villax | A61M 15/0045 128/203.15 |
| 2009/0320838 A1 | 12/2009 | Malhotra et al. | |
| 2010/0313886 A1* | 12/2010 | Wachtel | A61M 15/0028 128/203.15 |
| 2011/0259328 A1 | 10/2011 | Villax et al. | |
| 2014/0182587 A1* | 7/2014 | Dunne | A61M 15/0028 128/203.15 |
| 2015/0014428 A1 | 1/2015 | Rome | |

FOREIGN PATENT DOCUMENTS

| | | |
|---|---|---|
| WO | 199936116 | 7/1999 |
| WO | 2007132217 | 11/2007 |
| WO | 2013184951 | 12/2013 |

OTHER PUBLICATIONS

PT108426, Rule 141 Prior Art Search Results dated May 30, 2015, 1 page.

* cited by examiner

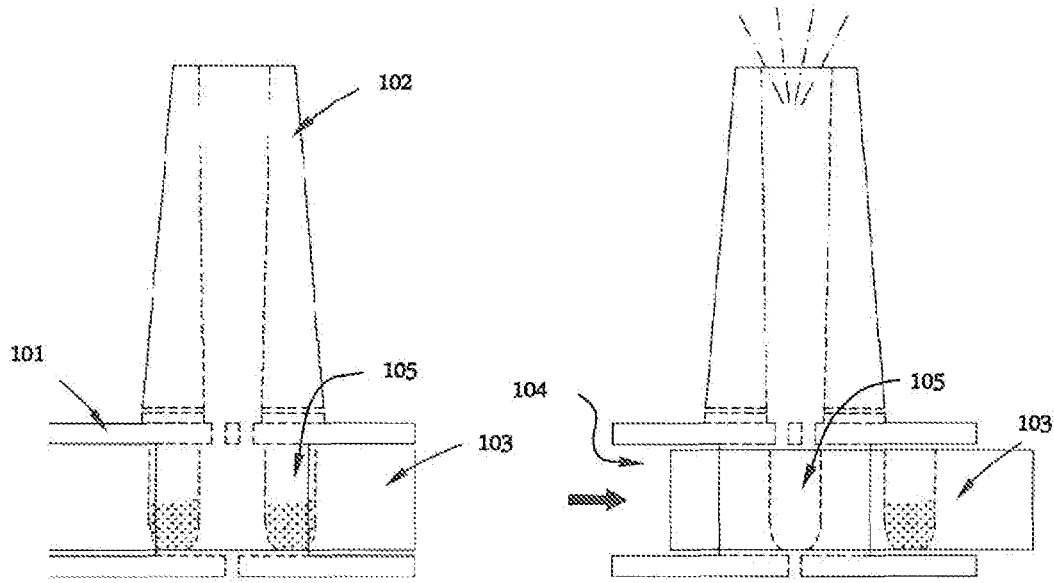
Fig. 1a
PRIOR ART
Fig. 1b
PRIOR ART
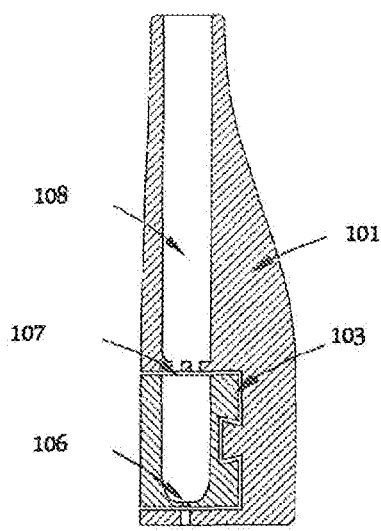
Fig. 1c
PRIOR ART

POWDER COMPARTMENT FOR HIGH DOSAGE DRUG DELIVERY

BACKGROUND OF THE INVENTION

1. Field of the Invention

The present invention describes a novel powder compartment for a single-use disposable pulmonary or nasal inhaler of simple construction, operation and low cost for the delivery of high dosages of pharmaceutical compounds.

Inhalers used for the delivery of pharmaceutical compounds have become widespread and include pressurized metered dose, nebulizers and powder-based inhalers. The latter category delivers the dose of medicinal powder using the energy generated by the patient's inspiratory effort and includes multi-use reservoir-based devices, re-usable devices supplied with unit-doses packaged in blisters, re-usable devices using unit-dose capsules loaded by the patient, and single-use disposable powder-based inhalers. The present invention is in this last category.

Powder-based inhalers have been used mainly for maintenance treatment of respiratory diseases such as asthma or the chronic obstructive pulmonary disease. However, single-use disposable devices have deserved considerable attention due to the need to treat situations were an infectious agent is being treated or is present in the mouth or airways and the elimination of the potential for inhaler contamination is thus required.

Furthermore, the effort to develop single-use disposable inhalers has also been fuelled by the growing interest in delivering to patients high payloads, in the range of 50 to 120 mg, of pharmaceutical compounds such as antibiotics, vaccines, proteins, peptides, insulin or other drugs systemically via the lung or nose through few, simple and intuitive interactions with the device. In such applications, pharmaceutical compounds that have been particle engineered by processing techniques such as spray drying or jet milling are normally characterized by high adhesion and cohesion properties resulting from low median particle size by volume, typically below 2 μm, in addition to low bulk density, typically in the range of 0.2 g/cm3-0.5 g/cm3.

Therefore, a major challenge is designing the mechanism for aerosolizing and dispersing large quantities, in the range of 50 to 120 mg, of highly cohesive and adhesive powders while minimizing the amount of powder retention in the device. In addition, a significant challenge is also the provision of deagglomeration mechanisms which ensure the break-up of such large quantities of highly agglomerated drug particles down to particles with an inhalable size of less than 5 μm while, simultaneously, preventing such large dose to be released in a very short period of time. Such sudden release may lead to the "powdery mouth" effect, throat irritation and large drug losses in the upper airways. The means for powerful aerosolisation and controlled powder deagglomeration and release is thus required by design.

Furthermore, the great majority of the patients requiring antibiotics, vaccines, proteins, peptides or other drugs in such applications are inhaler-naive and may not have any training in inhalation. It is thus required that the device be of extreme simplicity and intuitive to use. In addition, the developer of a disposable inhaler for high dosage drug delivery is also faced with the challenge of gaining competitive advantage through a reduction in the cost of the device, both through the use of the fewest number of components as possible and designing for fast assembly during high volume manufacturing.

2. Discussion of Prior Art

There is abundant prior art in the field of single-use disposable inhalers, but a disposable inhaler solving all the above requirements has not been provided yet. The present application is particularly directed at the inventive improvement of the inhaler described in PT103481.

Previously, as described in PT103481 and illustrated in FIG. 1a to 1c and 2a of the accompanying drawings, there was known a disposable inhaler comprising a body 101 including a mouthpiece 102 and a cartridge 103 mounted in an opening 104 provided in the body 101 and having at least one powder compartment 105. The powder compartment 105 had inlet holes 106 to admit air and outlet holes 107 to communicate with an inhalation channel 108 provided in the body 101. Furthermore, the cartridge 103 was made slidable relative to the body 101 by the patient, between a first position detailed in FIG. 1a where the compartment rear holes 106 were isolated and sealed, and a second position detailed in FIGS. 1b and 1c in which the compartment rear 106 and front 107 holes were aligned with the body inhalation channel 108, thus allowing the flow of air to disperse and entrain the powder through the mouthpiece and into the patient's mouth or nasal cavity and finally into the desired site of action. The construction disclosed in PT103481 allowed for a device with pre-filled unit doses of powder for patient convenience, disposable for reasons of safety and hygiene, simple for economic reasons and intuitive for ease of use by the patient. While this inhaler is being successfully marketed, tests indicate the maximum deliverable dose is in the region of 10-20 mg of powder.

Other single-use disposable inhalers are also already known in the prior art.

U.S. Pat. No. 5,797,392 discloses one of the simplest designs of a single-use disposable inhaler similar to a drinking straw. Although simple, the construction disclosed does not provide dispersion and deagglomeration mechanisms or features allowing the break-up of large quantities of highly cohesive drug particles and excipients down to the inhalable size while minimizing powder retention in the device.

U.S. Pat. Nos. 5,042,472, 5,239,991, 6,098,619 and WO pat. 2014/175815 disclose also other simple single-use and disposable devices apparently absent of major powder deagglomeration features and the constructions disclosed in the drawings are likely to cause the sudden release of powder leading to the undesirable "powdery mouth" and throat irritation effects.

U.S. Pat. Nos. 6,286,507, 2008/0190424 and US pat. 2009/0250058 disclose other single-use disposable inhaler constructions generally comprising a first body member including a powder compartment and a second body member which are closely fit to form an inhaler body with an outlet, where the two body member are separated by a strip or tape which exposes the powder compartment to air when pulled away from the inhaler body. However, the constructions presented rely on simple throughflows that are absent of flow patterns into the powder compartment thus preventing the application of powerful dispersion and deagglomeration forces on powders for its effective detachment from the compartment's walls, which is particularly important for the successful delivery of large payloads of cohesive powders.

U.S. Pat. No. 6,941,947 discloses another single-use dry powder inhaler having a dispersion chamber, a blister supported and adjacent to the dispersion chamber, a mouthpiece and a hinged cover. The opening movement of the hinged cover causes the blister to open and an airflow path is formed that extends under the blister and into the dispersion chamber. However, the drawings disclosed in this patent show also an apparent absence of powerful flow patterns for dispersion and deagglomeration of large payloads of powder, a construction comprising at least 4 unique components and a non-trivial assembly sequence, both adding to total manufacturing cost.

There is therefore the need for a single-use disposable device which achieves the functionalities of the disposable inhalers described above with effective aerosolisation and deagglomeration mechanisms for large payloads of very cohesive powers, in the range of 50 to 120 mg, that minimizes powder retention, that is simple and intuitive to use and that can be manufactured at a very low cost.

SUMMARY OF THE INVENTION

The present invention seeks to provides a novel powder compartment for a disposable inhaler that improves the construction disclosed in PT103481 for the dispersion and deagglomeration of large payloads, in the range of 50 to 120 mg, of inhalation powders characterized by high cohesive and adhesive properties, resulting from a low median particle size by volume, typically below 2 μm, while maintaining an inhaler that is simple and intuitive to use and that can be manufactured at a very low cost. Furthermore, the present invention seeks to provide a powder compartment for a disposable inhaler that minimizes the powder retention in the device during the dispersion of large powder payloads while retaining an improved deagglomeration performance leading to an improvement of the dose delivered to the patient's respiratory system.

When testing with a high payload, in the range of 80 to 100 mg, of inhalable amorphous composite particles composed of 80% trehalose and 20% leucine produced by spray drying, used as model drug particles representative of the typical high cohesive-adhesive behaviour found in powders for high dosage applications, we initially scaled up the existing construction disclosed in PT103481. This scale-up was made linearly in every dimension by 20% to increase the powder compartment capacity for accommodating such payloads of powders with typical bulk density in the range of 0.2 g/cm3-0.5 g/cm3. However, at a pressure drop of 4 kPa, the emitted mass from the device calculated from the mass of powder deposited at each stage of a cascade impactor was about 50%. It was clear that dispersive and aerosolisation characteristics of an enlarged construction as disclosed in PT103481 were not going to lead to an effective large dose disposable inhaler.

Subsequently, in order to increase the dispersive and aerosolisation power of the construction disclosed in PT103481, additional symmetrical air vents providing supplementary air flow to the powder compartment were introduced and the new construction was tested with the same payload of the model drug particles. At a pressure drop of 4 kPa, the emitted mass from the device calculated from the accumulated mass of powder deposited at each stage of a cascade impactor was increased to approximately 65% of the nominal or starting dose. This performance was still not adequate and it was clear that just an increase of flow rate passing through the powder compartment, provided by symmetrically disposed air vents was not going to lead to an effective large dose disposable inhaler.

The inventive solution was given by placing the air vents in a disposition that maximizes turbulence and aerosolization, in a new geometry. The powder compartment disclosed in PT103481 needed to be reinvented to create novel, effective dispersive and aerosolisation dynamics leading to low powder retention and a disposable inhaler capable of operating with large payloads of powders characterized by challenging cohesion-adhesion properties. To attain such purpose, the existing powder compartment which was provided with a an air slit at the bottom and a large outlet at the top, was constructed with additional lateral vents, forming pairs of lateral vents, placed at various heights of the powder compartment, with each vent forming the pair of vents offset relative to each other to provide a non-tangential admission of air. The new construction was tested with the same payload of the model drug particles representative of high dosage applications. At a pressure drop of 4 kPa, the emitted mass from the new device calculated from the mass of powder deposited at each stage of a cascade impactor was approximately 91% and powder retention within the compartment itself was observed to be residual. The results indicate that the novel design of the powder compartment provides a high rate of drug delivery of challenging powders characterized by low density and high cohesive-adhesive properties.

The table data indicates the improvement in performance in gravimetric emitted dose, expressed in percent of emitted dose, and the variability of performance expressed in terms of percent relative standard deviation.

| Powder compartment | Body bottom inhalation channel inlet | Emitted Mass (%) | Emtitted Mass RSD (%) |
|---|---|---|---|
| Scale-up PT103481 | Multiple orifices, 3 × 3 grid arrangement | 51.0 | 44.8 |
| Scale-up PT103481 with additional symmetrical air vents | Multiple orifices, 3 × 3 grid arrangement | 69.0 | 29.3 |
| Scale-up PT103481 with additional symmetrical air vents | Single orifice | 80.5 | 5.2 |
| Scale-up PT103481 with additional symmetrical air vents | Multiple orifices, 2 × 2 grid arrangement | 85.0 | 5.4 |
| Scale-up PT103481 with additional air vents in offset | Multiple orifices, 3 × 3 grid arrangement | 91.2 | 1.4 |
| Scale-up PT103481 with additional air vents in offset | Single orifice | 88.5 | 4.3 |
| Scale-up PT103481 with additional air vents in offset | Multiple orifices, 2 × 2 grid arrangement | 92.9 | 1.1 |

The present invention accordingly provides a dry powder inhaler according to claim 1.

More particularly, the inhaler of the present invention comprises two plastic-injected components as in PT103481: a body and a cartridge. The body and cartridge are locked together after assembly to form an integral and functional inhaler.

As in PT103481, the inhaler body is provided with a mouthpiece or nosepiece, an opening shaped for receiving and holding in place a cartridge and an inhalation channel for providing fluid communication between the patient's mouth or nose when engaged with the mouthpiece or nosepiece and the assembled cartridge. One or more body side inlets are provided to admit air directly from the atmosphere to the inhalation channel. Optionally a body bottom opening is included in the bottom wall of the body opening shaped for receiving the cartridge, to allow the admission of air from the atmosphere into the cartridge powder compartment when the cartridge is moved into the inhalation position. One or more rails are also provided in the side walls of the body opening shaped for receiving the cartridge where one or more pins of the cartridge engage to provide the means for allowing the sliding movement of the cartridge relative to the body and limit its sliding travel.

As found in PT103481, the cartridge includes at least one powder compartment, preferably two, that are built or moulded therein, which are always isolated from each other and are of tapered cylindrical or near-cylindrical shape with rounded extremities absent of sharp angles, such as spherical, oval and the like to minimize powder retention during and after inhalation. The cartridge comprising the powder compartments is made movable when mounted in the body opening. This movement is allowed through the engagement of one or more cartridge pins with the rails provided in the body which allow the controlled sliding of the cartridge relative to the body. In addition, there is at least one compartment bottom slit for the admission of air that is of very small size, between 0.1 and 2 mm in width, preferably 1 mm or less in width, and is tapered in the direction of the compartment to create a funnel that blocks the flow of powder under gravity and other forces. Each powder compartment comprised also a compartment outlet, normally of the same or similar diameter as the compartment itself, to allow normal filling and automated high-speed filling of the powder and to allow fluid communication with the body inhalation channel through the body bottom inhalation channel inlet when the cartridge is moved into the inhalation position.

However, the inhaler of the present application includes new features not found in the inhaler described in PT103481 or in the prior art and they are now detailed.

In this new inhaler, the cartridge powder compartment further comprises at least two compartment vents for the admission of air, at least one of which is a lateral vent, preferably two or four forming pairs of lateral vents being present, where each of said pairs is included in opposite ends of the powder compartment and each vent forming the pair is offset relative to the other to provide a non-tangential admission of air, and being the lateral vents of very small size, between 0.1 and 2 mm in width, preferably 1 mm or less in width, to minimize powder leakage under vibration or other forces. The or each side vent preferably tapers inwards towards the inner surface of the compartment wall so as to funnel the air as it is drawn through the vent into the compartment, thereby increasing aerodynamic efficiency and facilitating manufacturing.

Furthermore, the new cartridge powder compartment comprises at least one compartment protruding rim or similar construction that provides close mechanical contact and interference with the top or bottom walls, or both, of the body opening shaped for mounting the cartridge, and at least one pair of compartment protruding rims or similar construction at the side inlets that provides close mechanical contact and interference with the side walls of the body opening shaped for mounting the cartridge, to ensure sealing of the powder compartment while allowing a low frictional sliding movement of the cartridge.

Figure 6A:
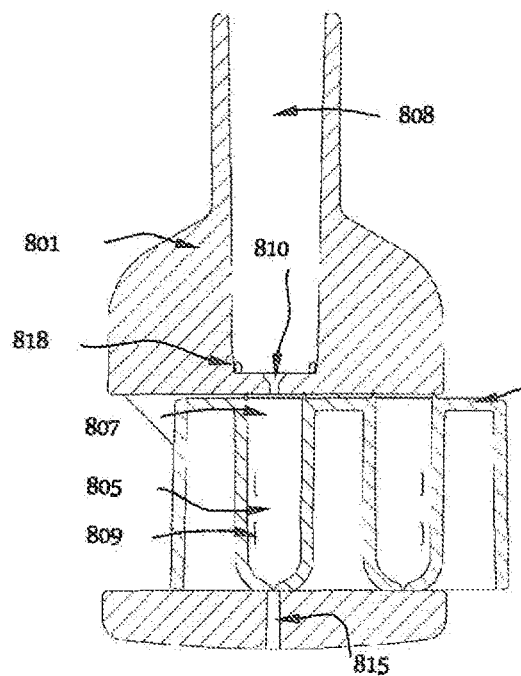
Figure 6B:
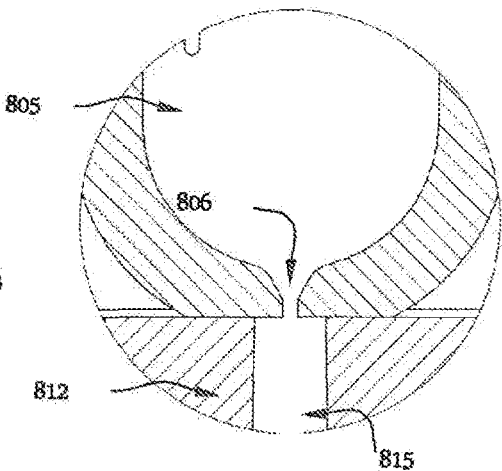
Figure 6C:
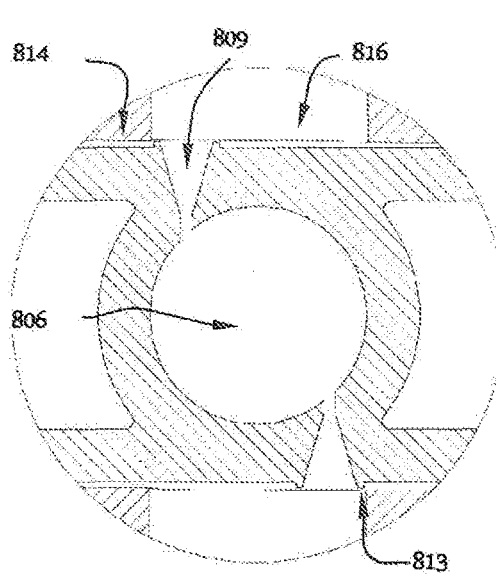
Figure 6D:
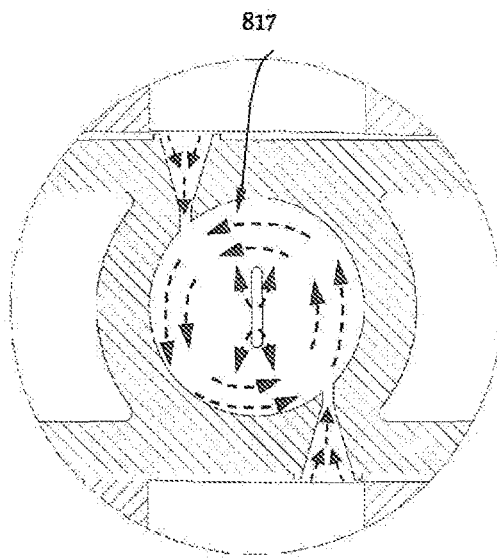

Two additional features are found in the inhaler of the present invention which are not present in the inhaler of PT103481. One is that the inhaler body of the present invention further comprises a bottom inhalation channel inlet, included in the top wall of the body opening shaped for receiving the cartridge, where said bottom inhalation channel inlet comprises a single orifice or multiple orifices of any shape or multiple orifices of any shape arranged to form a structured grid, that jointly provide a sharp geometric constriction in the fluid channel passage area where the geometric constriction area ranges between 0.3 and 0.99 of the cartridge powder compartment outlet cross section area, preferably between 0.8 and 0.98.

The other additional feature in this new inhaler is that the inhaler body includes one or more body side openings, included in the side walls of the body opening shaped for receiving the cartridge, to allow the admission of air from the atmosphere into the cartridge powder compartment when the cartridge is moved into the inhalation position.

The inhaler body and the cartridge can be made by injection-moulding of any suitable material for pharmaceutical use such as polyethylene (PE), polypropylene (PP), polysulfone (PSU), acrylonitrile butadiene styrene (ABS), polymethylmetacrilate (PMMA), polycarbonate (PC), polypropilene oxide (PPO), polybutylene terephthalate (PBT) polyethylene terephthalate (PET), liquid crystal polymer (LCP), polyethyleneimine (PEI), polyphenylenesulphide (PPS). Material selection should be made to maximize compatibility with the powder to be contained and delivered, minimize retention during inhalation and degradation during storage and allow transparency if possible.

During assembly, after filling the cartridge powder compartments with a unit dose of powder, the cartridge is inserted into the body through the opening shaped for mounting the cartridge. The powder compartment enters into the contact with the top, bottom and side walls of the body opening providing a close fit and sealing of the compartment. In addition, when the cartridge is mounted the pins engage with the body rails and allow the sliding movement into the cartridge storage position.

In the storage position, the powder compartments are offset relative to the inhalation channel provided in the body. Furthermore, the powder compartment bottom inlet slits are in contact with and fully blocked by the bottom wall of the body opening for mounting the cartridge. In addition, the powder compartment lateral vents are in contact with and fully blocked by the side walls of the body opening for mounting the cartridge. Therefore, the powder unit dose is effectively sealed inside its compartment and close contact with the opening bottom and side walls prevents the powder compartment contents from escaping. In its storage position, the inhaler is then ready for packaging, desirably in a foil or aluminium pouch, or pouch or packaging of any other suitable material and under low or equilibrium humidity conditions.

During use of the inhaler of the present invention, the patient removes it from its packaging and accesses the inhaler with the cartridge in the storage position. The patient then pushes into the cartridge to slide it into the inhalation position. At this position, the powder compartment bottom inlet slit becomes aligned with the air inlet provided in the bottom wall of the body opening for allowing air admission. Furthermore, at this position, the powder compartment lateral vents become aligned with the side openings/windows provided in the side walls of the body opening for allowing air admission. Also, at this position, the powder compartment outlet becomes aligned with the bottom inlet of the inhalation channel that is included in the top wall of the body opening.

When the cartridge has traveled into the inhalation position, the patient then inhales a first dose, according to the instructions for use, and airflow is created across the device. Air is first able travel through the body bottom air inlet and into the powder compartment through the compartment bottom inlet slit effectively inducing a turbulent jet to disperse the particles there contained.

In addition, air is also able to travel through the body side opening/window into the powder compartment through compartment lateral vents or through the pair of compartment lateral vents, which provide admission of supplementary air to allow an increase in the turbulence kinetic energy within the compartment that is available for dispersion and deagglomeration of the drug particles. Moreover, the non-tangential air admission through the compartment lateral vents induces a turbulent vortex that confines the bottom turbulent jet and generates a high velocity magnitude near to the compartment walls and thus provide the means to effectively reduce powder retention in the device during inhalation.

The turbulent and swirling air flow generated in the compartment thus allows the particles to be dispersed and travel through the powder compartment outlet and into the bottom inhalation channel inlet comprised in the body. There, the sudden cross sectional reduction that is constructed through the body inhalation channel inlet design allows further deagglomeration and break-up of the particle clusters through impaction on the surrounding inlet walls and through the generation of high shear forces and turbulence kinetic energy across the inlet passage itself.

The flow of air with entrained particles then enters the body inhalation channel and the supplementary air flow provided through the body side inlets induces additional channel turbulence leading to further dispersion and deagglomeration of the particles, for entrainment and final deposition in the intended site, in the lung or in the nasal cavity, depending on the application. If there is a second powder compartment comprised in the cartridge, the patient then moves it to the inhalation position and inhales a second time, repeating the maneuver as often as there are compartments. A benefit of all of these inlets and lateral vents is that inhalation may be complete with one single inhalation attempt.

In addition to providing the turbulent kinetic energy for powder dispersion and deagglomeration, the inlets, slits and vents provided in the powder compartment as well as those in the body allow the design of the inhaler resistance and aerodynamic profile which in turn determines the comfort experienced by the patient during inhalation.

This novel construction allows the dispersion and deagglomeration of large payloads of cohesive inhalation powders while minimizing powder retention and while maintaining an inhaler that is simple and intuitive and maintaining the part count to two unique components assembled through a single and simple assembly step, both contributing to low manufacturing cost and consequent economic advantage.

Based on these advantages, it is one inventive feature of the present application that the cartridge powder compartment of tapered cylindrical or near-cylindrical shape comprises at least one bottom inlet slit and at least one side/lateral vent, preferably two or four forming pairs of lateral vents, which are respectively blocked and sealed by the body opening bottom and side walls when the cartridge is in the storage position, and which become available for the admission of air into the compartment when the cartridge is aligned and placed into the inhalation position.

It is also an inventive feature of the present application that the cartridge powder compartment lateral vents are included in opposite sides of the powder compartment and each vent forming one pair is offset relative to the other to provide a diagonal, non-tangential admission of air, thus providing the means for the admission of supplementary air flow inducing a turbulent vortex in the compartment that increases the turbulent energy available for the dispersion and deagglomeration of drug particles there contained, and that increases the near-wall velocities in the compartment for the reduction of powder retention during inhalation.

It is also an inventive feature of the present application that the cartridge powder compartment lateral vents are of very small size, between 0.1 and 2 mm in width, preferably 1 mm or less in width, to increase air vent velocities for the application of high dispersive forces on particles there contained, and are further tapered towards the inner surface of the compartment to increase aerodynamic efficiency and allow manufacturing through standard injection moulding processes.

It is also an inventive feature of the present application that the cartridge powder compartment has at least one pair of compartment protruding rims or similar construction at the side inlets that provides close mechanical contact and interference with the side walls of the body opening shaped for mounting the cartridge, to ensure sealing of the powder compartment while allowing a low frictional sliding movement of the cartridge.

It is also an inventive feature of the present application that the body inhalation channel comprises a bottom inlet included in the top wall of the body opening shaped for receiving the cartridge where said bottom inhalation channel inlet comprises a single orifice or multiple orifices of any shape or multiple orifices of any shape arranged to form a structured grid, that jointly provide a sharp geometric constriction in the fluid channel passage area where the geometric constriction area ranges between 0.3 and 0.99 of the cartridge powder compartment outlet cross section area, preferably between 0.8 and 0.98, that allows further deagglomeration and break-up of the particle clusters dispersed within the powder compartment through impaction on the surrounding inlet walls and through the generation of high shear forces and turbulence kinetic energy across the inlet passage.

BRIEF DESCRIPTION OF THE DRAWINGS

FIGS. 1*a* to 1 *c* and 2*a* show a prior art inhaler;

FIGS. 2*b* to 2*g* show perspective and side views of multiple embodiments of the powder compartment according to the invention;

FIG. 3*a* shows a longitudinal sectional detailed view of the cartridge powder compartment outlet when the cartridge is moved into the inhalation position of and body inhalation channel bottom inlet according to the invention;

FIG. 3*b* to 3*d* show top views of multiple embodiments of the body inhalation channel bottom inlet according to the invention;

FIG. 4*a* to 4*b* show perspective views of the inhaler according to the invention when the powder cartridge is respectively in the storage and inhalation position;

FIG. 5*a* shows a longitudinal sectional view of the inhaler according to the invention when the powder cartridge is in the storage position;

FIG. 5*b* shows a longitudinal sectional detailed view of the powder cartridge bottom inlet according to the invention when the cartridge is in the storage position;

FIG. 5*c* shows a transversal sectional view of the inhaler according to the invention when the powder cartridge is in the storage position;

FIG. 6*a* shows a longitudinal sectional view of the inhaler according to the invention when the powder cartridge has been moved into the inhalation position;

FIG. 6b shows a longitudinal sectional detailed view of the powder cartridge bottom inlet according to the invention when the cartridge has been moved into the inhalation position;

FIG. 6c to 6d show transversal sectional detailed views of the inhaler according to the invention when the powder cartridge has been moved into the inhalation position;

DETAILED DESCRIPTION OF THE INVENTION

Referring to the drawings, numbered sequentially after the word "FIG.", like numerals indicate like parts, and each of the embodiments is identified with series of numbers where the number of hundreds is the number of the embodiment (1xx to 8xx) and the equivalent feature in each of the embodiments has the same number xx.

Referring to FIG. 2 which shows multiple embodiments of the powder compartment according to the invention, there is shown in FIG. 2a the first embodiment of the cartridge powder compartment 105 of tapered cylindrical or near-cylindrical shape comprising at least one bottom inlet slit 106. FIG. 2b shows a second embodiment of the cartridge powder compartment 205 of tapered cylindrical or near-cylindrical shape according to the invention comprising one bottom inlet slit 206 and at least one lateral vent 209. FIG. 2c shows a third embodiment of the cartridge powder compartment 305 according to the invention comprising one bottom inlet slit 306 and a pair of compartment lateral vent 309 included in opposite sides of the powder compartment 305. FIG. 2d shows a fourth embodiment of the cartridge powder compartment 406 according to the invention comprising one bottom inlet slit 406 and a pair of compartment lateral vent 409 included in opposite sides of the powder compartment 405 where each lateral vent 409 forming the pair is longitudinally offset relative to the other to allow a non-tangential admission of air into the powder compartment 405. FIG. 2e shows a fifth embodiment of the cartridge powder compartment 505 according to the invention comprising one bottom inlet slit 506 and a pair of compartment lateral vent 509 included in opposite sides of the powder compartment 505 where each lateral vent 509 forming the pair is longitudinally and vertically offset relative to the other to allow a diagonal and non-tangential admission of air into the powder compartment 505. FIG. 2f shows a sixth embodiment of the cartridge powder compartment 605 according to the invention comprising one bottom inlet slit 606 and multiple pairs of compartment lateral vent 609 included in opposite sides of the powder compartment 605 where each lateral vent 609 forming one of the pairs is longitudinally and vertically offset relative to the other to allow a diagonal and non-tangential admission of air into the powder compartment 605. FIG. 2g shows a seventh embodiment of the cartridge powder compartment 705 according to the invention comprising multiple pairs of compartment lateral vent 709 included in opposite sides of the powder compartment 705 where each lateral vent 709 forming one of the pairs is longitudinal and vertically offset relative to the other to allow a diagonal and non-tangential admission of air into the powder compartment 705.

Figure 3A:
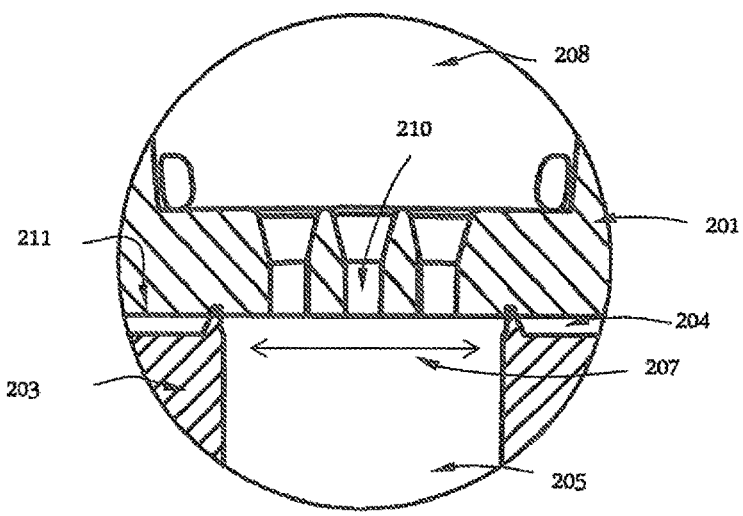
Figure 3B:
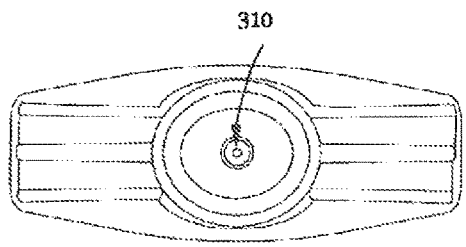
Figure 3C:
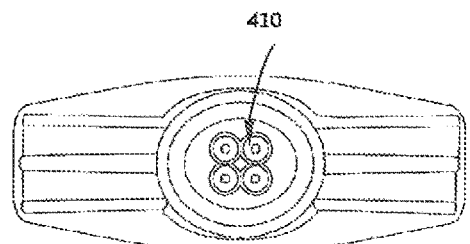
Figure 3D:
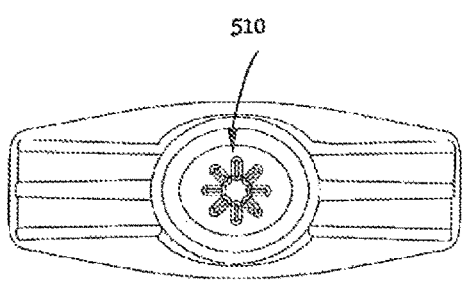
Figure 3E:
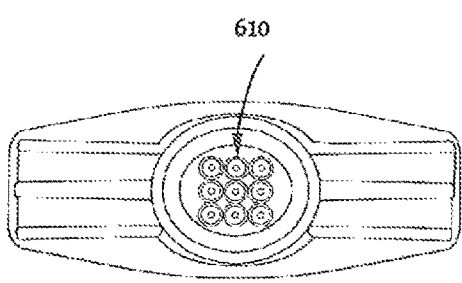
Figure 4A:
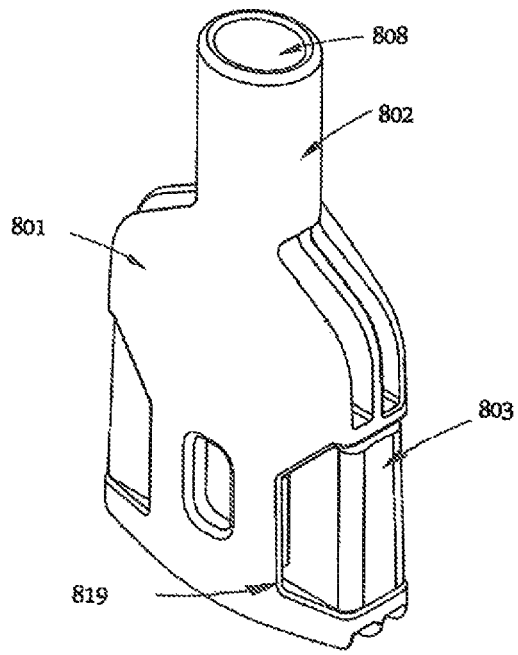
Figure 4B:
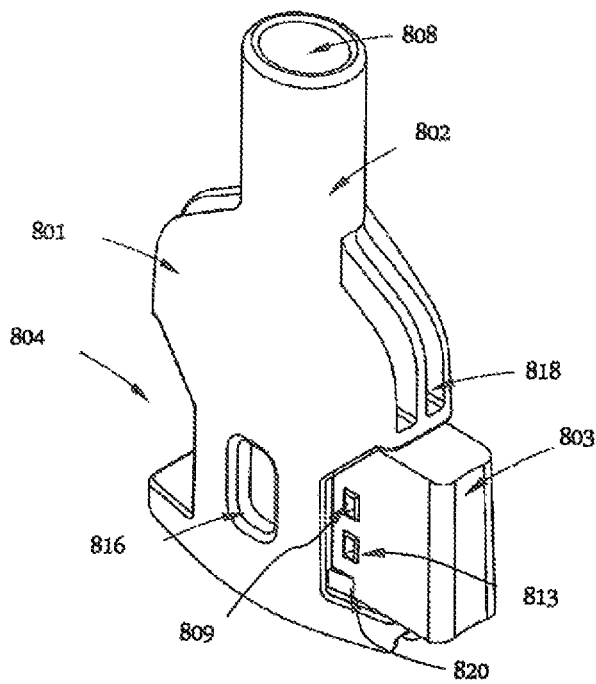
Figure 5A:
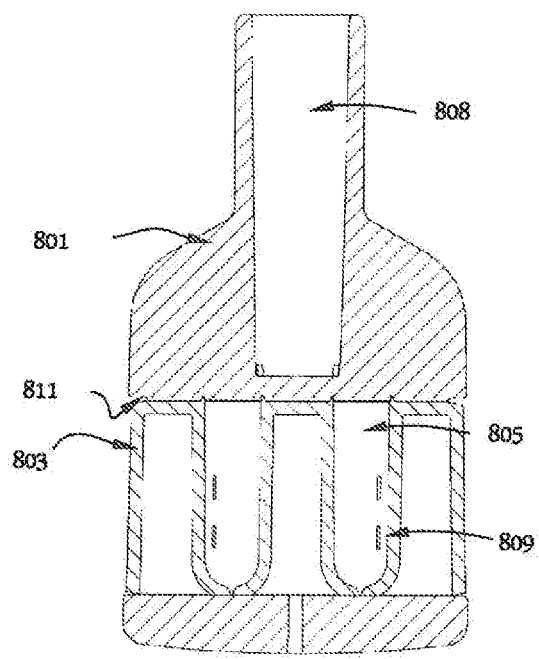
Figure 5B:
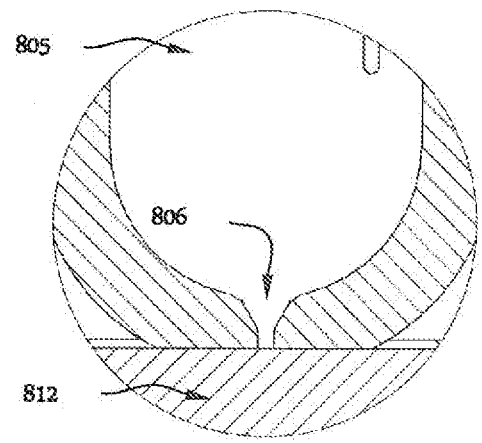
Figure 5C:
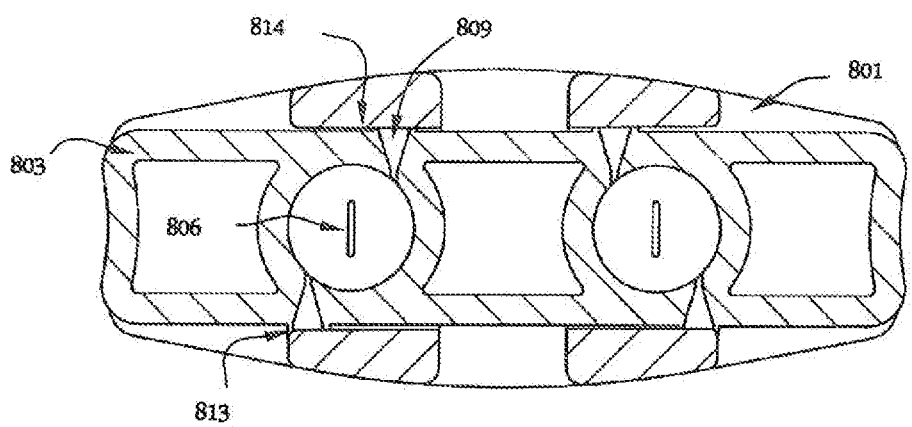

FIG. 3a shows a detailed longitudinal sectional view of the powder cartridge 203 including a powder compartment 205 according to the invention when the cartridge 203 is moved into the inhalation position and is aligned with a body inhalation channel 208 which allows the fluid communication between a powder compartment outlet 207 and a body inhalation channel bottom inlet 210 included in a top wall 211 of a body opening 204 for receiving the cartridge 203. There is also shown in FIG. 3*a* that the inhalation channel bottom inlet 210 comprises one or more orifices included in the top wall 211 of the body opening 204 that jointly provide a sudden geometric obstruction of the channel passage area in relation to the powder compartment outlet 207 cross sectional area. Moreover, FIGS. 3*b* to 3*d* show top views of additional embodiments of the inhalation channel bottom inlet 210, each similarly providing a sudden obstruction of passage area in relation to the powder compartment outlet 207 cross section area. FIG. 3*b* shows an embodiment of the inhalation channel bottom inlet 310 comprising a single circular orifice, while FIG. 3*c* shows an embodiment including an inhalation channel bottom inlet 410 formed of multiple circular orifices. FIG. 3*d* shows an embodiment of an inhalation channel bottom inlet 510 formed of multiple orifices with non-circular shape. FIG. 3*e* further depicts an embodiment of an inhalation channel bottom inlet 610 comprising multiple orifices forming a structured grid.

Referring next to FIGS. 4, 5 and 6, there is shown an inhaler embodiment according to the invention in two different operational configurations. In FIG. 5*a*, a powder cartridge 803 is assembled into an opening 804 shaped for receiving it in the body component 801 and the cartridge 803 is the storage position. As shown in detail in FIGS. 5*b* and 5*c*, when the powder cartridge 803 is in it storage position, a compartment bottom inlet slit 806 is closed by smooth bottom walls 812 of the body opening 804 and a powder compartment lateral vent 809 is closed by the mechanical interference between compartment side protruding rims 813 and smooth side walls 814 of the body opening 804 so that the powder is blocked inside the compartment 805.

In FIG. 6*a*, the powder cartridge 803 has been moved from the storage position shown in FIGS. 5*a* to 5*c* to the inhalation position allowing one of the powder compartments 805 to become aligned with the body inhalation channel 808. In this position. FIG. 6*b* details that air admission is allowed from atmospheric conditions through a body bottom opening 815 shaped in the body bottom walls 812 into the powder compartment 805 through the compartment bottom inlet slit 806. Also in this position, FIG. 6*c* shows in detail that supplementary air admission is also allowed from atmospheric conditions through the body side opening window 816 shaped in the body side walls 814 into the powder compartment 805 through the compartment lateral vent 809. Furthermore, FIG. 6*a* shows also that when one of the powder compartments 805 is moved into the inhalation position, fluid communication is established between a powder compartment outlet 807 and a body inhalation channel 808 through the body inhalation channel bottom inlet 810, which provides a sudden reduction of passage area relative to the powder compartment outlet 807 cross section area as depicted in FIG. 6*a*.

When the powder cartridge 803 is in the inhalation position and the patient's mouth or nose is engaged with a body mouthpiece 802, the patient's inspiratory effort creates a suction that forces the air to travel through the body bottom inlet 815 and the powder compartment bottom inlet slit 806 inducing a bottom turbulent jet and simultaneously through the body side opening windows 816 and the powder compartment lateral vent 809 inducing a turbulent vortex confining the bottom turbulent jet, which generates a turbulent and swirling air flow pattern 817 shown in FIG. 6*d* through the powder compartment. This flow allows the drug particles to be dispersed while minimizing powder retention and travel through the powder compartment outlet 807 and into the bottom inhalation channel 810, where the sharp geometric constriction of fluid passage area allows further deagglomeration and break-up of the drug particle clusters, and finally into the body inhalation channel 808 and then into the mouth (or nose) and finally into the intended site of treatment such as the nasal cavity or the lung. Additional supplementary air flow is also provided to the body inhalation channel 808 through the body side inlets 818 to provide additional dispersive forces as well as a comfortable inhalation and to maximize the entrainment capability of the air.

EXAMPLE

Figure 2F:
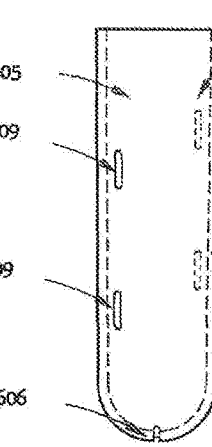
Figure 2G:
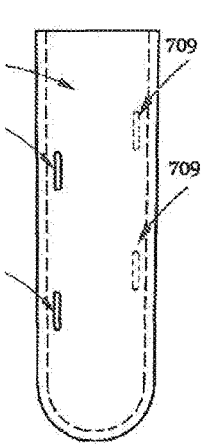

An inhaler embodiment according to the present invention has been tested in vitro to determine its aerodynamic profile as well as its powder dose delivery characteristics. The inhaler embodiment comprised a powder compartment according to the present invention that included one bottom inlet slit and four lateral vents with pairs of lateral vents in offset configuration as shown in FIG. 2f. The inhaler embodiment comprised a body inhalation channel bottom inlet, included in the top wall of the body opening, including multiple orifices arranged to form a structured grid that jointly provided a sudden obstruction of channel passage area where the obstruction area was approximately 0.85 of the compartment outlet cross section area.

An experimental inhalation powder comprising inhalable amorphous spherical composite particles composed of 80% trehalose and 20% leucine was produced by spray drying. The composite particle spry dried powder was produced with a median particle size by volume (Dv50) of approximately 2 µm leading to high cohesiveness and adhesiveness properties. The particle size, cohesive and adhesive properties of the powder were representative of powders produced by spray drying for applications of high dosage drug delivery to the lungs.

The inhaler was hand filled with 80 mg of composite particle spray dried powder (40 mg per compartment), under controlled conditions of temperature and relative humidity (T<25° C. and % RH<30%), inside a glove box conditioned with nitrogen and using an appropriate analytical balance. The inhaler was then tested at a flow rate of 42 litres per minute and at a pressure drop of 4 kPa on an Andersen cascade impactor (Graseby Andersen. Smyrna, Ga.), actuated once to allow a volume of 4 litres of air to pass through the device, and the mass of powder deposited at each stage of the cascade impactor was quantified using gravimetric methods. From these data, the emitted mass and the fine particle mass were calculated, where the emitted mass was the sum of all masses collected from each of the impactor stages, including the inductor throat, and the fine particle mass was the mass of powder collected below the 5 µm cut-off point. High dispersive and aerosolisation efficiency leads to a high emitted mass from the inhaler. In addition, the higher the fine particle mass, the higher the delivered lung dose is expected to be. The results are summarized in the following table:

|  | Delivery performance |
|---|---|
| Emitted mass (EM) | 73.4 mg |
| Fine particle mass ($FPM_{5\mu m}$) | 29.9 mg |
| Fine particle fraction ($FPM_{5\mu m}$/EM) | 40.7% |

This data indicates that the inhaler embodiment according to the present invention is capable of effectively dispersing and delivering large doses, in the range of 50 to 120 mg, of an inhalation powder, under inspiratory effort conditions which are compatible with the ability of patients.

The invention claimed is:

1. A dry powder inhaler suitable for pulmonary or nasal delivery, comprising an inhaler body and a cartridge; the inhaler comprising:
    (a) the inhaler body comprising a mouthpiece, a bottom channel inlet, an inhalation channel for providing fluid communication between the patient's mouth when engaged with the mouthpiece and the bottom channel inlet, at least one side inlet for allowing direct air admission from atmosphere into the inhalation channel; an inhaler body opening formed therein and defined between opposing top and bottom walls and opposing side walls, said inhaler body opening having at least one open end by means of which the cartridge is insertable into the opening and having at least one air inlet opening for admitting air into the inhaler body opening, means for guiding movement of the cartridge in the inhaler body opening relative to the body and control the cartridge travel from a storage position into an inhalation position; wherein the cartridge;
    (b) the cartridge being shaped for engagement in the inhaler body opening and having at least one substantially cylindrical powder compartment formed therein for carrying a powder-based medicament, and at least one air inlet vent; the powder compartment having an outlet which allows fluid communication with the body inhalation channel through the body bottom channel inlet and at least one pin for engaging with the body guiding movement means; wherein the cartridge is slidable within the body between the storage position in which the at least one air inlet vent of the cartridge is substantially sealed by the inhaler body such that there is no fluid communication to the cartridge, to the inhalation position, in which the or each air inlet vent of the cartridge is substantially aligned with an associated air inlet opening of the inhaler body such that there is fluid communication between the inlet opening of the inhaler body, the or each air inlet vent of the cartridge, the cartridge top outlet and the mouthpiece channel; wherein the cartridge having the at least one inlet vent includes at least two air inlet vents, at least one of which is a lateral air inlet vent and the inhaler body has an air inlet opening associated with each of the air inlet vents of the cartridge which allow admission of air from the atmosphere into the cartridge powder compartment when the cartridge is in the inhalation position; and the inhaler body bottom channel inlet further comprising at least one orifice which forms a sharp constriction in the fluid flow path from the cartridge powder compartment outlet into the inhalation channel when the powder cartridge is moved into the inhalation position.

2. The dry powder inhaler of claim 1, wherein the at least two air inlet vents of the cartridge includes a bottom inlet slit; and wherein the inhaler body includes a bottom opening which aligns with the bottom inlet slit when the cartridge is in the inhalation position.

3. The dry powder inhaler of claim 1, wherein the at least two air inlet vents of the cartridge includes at least one pair of lateral air inlet vents formed in the side walls of the cartridge: and wherein the air inlet openings of the inhaler body include at least one pair of side openings formed in the side walls of the body opening, each side opening aligning with at least one associated lateral air vent of the cartridge when the cartridge is in the inhalation position.

4. The dry powder inhaler of claim 3, wherein the or each pair of lateral air vents are located on opposite sides of the compartment and the lateral air vents forming each pair are offset relative to each other so as to allow a non-tangential admission of air.

5. The dry powder inhaler of claim 1, wherein each cartridge powder compartment lateral vent has a width of between 0.1 and 2 mm.

6. The dry powder inhaler of claim 5, wherein each cartridge powder compartment lateral vent has a width of less than 1 mm.

7. The dry powder inhaler of claim 1, wherein each side opening in the inhaler body is associated with a plurality of lateral vents.

8. The dry powder inhaler of claim 1, wherein each cartridge powder compartment lateral vent tapers inwards towards the inner surface of the compartment so as to funnel the air as it passes through the vent into the compartment.

9. The dry powder inhaler of claim 1, wherein the inhaler body bottom channel inlet includes a plurality of orifices.

10. The dry powder inhaler of claim 9, wherein said plurality of orifices are arranged to form a structured grid.

11. The dry powder inhaler of claim 1, wherein cartridge powder compartment includes a lateral protrusion in the area of the or each air inlet opening that provides mechanical contact and inference with top, bottom and side walls of the body opening when the cartridge is in the storage position so as to seal each said air inlet opening.

12. The dry powder inhaler of claim 1, wherein the inhaler body inhalation channel bottom inlet provides a geometric constriction in the fluid channel passage area, the cross-sectional area of which constriction is between 30% and 99% of the powder compartment outlet cross section area.

13. The dry powder inhaler of claim 12, wherein the cross-sectional area of constriction is between 80% and 98% of the powder compartment outlet cross section area.

* * * * *